(12) United States Patent
Zhao et al.

(10) Patent No.: US 11,116,433 B2
(45) Date of Patent: Sep. 14, 2021

(54) ECG SIGNAL COLLECTION AND WEARABLE APPARATUS

(71) Applicant: Hefei Huami Micro-Electronics Co., Ltd., Anhui (CN)

(72) Inventors: Yajun Zhao, Anhui (CN); Jixiang Su, Hefei (CN)

(73) Assignee: Hefei Huami Micro-Electronics Co., Ltd., Anhui (CN)

( * ) Notice: Subject to any disclaimer, the term of this patent is extended or adjusted under 35 U.S.C. 154(b) by 1142 days.

(21) Appl. No.: 15/609,146

(22) Filed: May 31, 2017

(65) Prior Publication Data
US 2017/0258356 A1    Sep. 14, 2017

Related U.S. Application Data

(63) Continuation of application No. PCT/CN2017/000071, filed on Jan. 3, 2017.

(30) Foreign Application Priority Data

Jan. 29, 2016 (CN) .......................... 201610074311.1

(51) Int. Cl.
*A61B 5/282* (2021.01)
*A61B 5/00* (2006.01)
(Continued)

(52) U.S. Cl.
CPC ............ *A61B 5/282* (2021.01); *A61B 5/0006* (2013.01); *A61B 5/316* (2021.01); *A61B 5/318* (2021.01);
(Continued)

(58) Field of Classification Search
CPC . A61B 5/0006; A61B 5/0402; A61B 5/04028; A61B 5/6886; A61N 1/0492; A61N 2001/083
See application file for complete search history.

(56) References Cited

U.S. PATENT DOCUMENTS

2010/0076331 A1    3/2010 Chan et al.
2012/0101396 A1*   4/2012 Solosko ............... A61B 5/0432
                                                  600/509
(Continued)

FOREIGN PATENT DOCUMENTS

CN    1111121 A    11/1995
CN    2848115 Y    12/2006
(Continued)

*Primary Examiner* — Eun Hwa Kim
(74) *Attorney, Agent, or Firm* — Young Basile Hanlon & MacFarlane, P.C.

(57) ABSTRACT

A wearable apparatus and a method for ECG signal collection includes: a main body, including a first ECG sensor electrode provided on a side of the main body away from a wearing position of an individual and a second ECG sensor electrode provided on a side of the main body close to the wearing position, a securing portion, including a third ECG sensor electrode provided on a side of the securing portion away from the wearing position, and an ECG sensor, provided in the main body and configured to: electrically connect to the first ECG sensor electrode and the second ECG sensor electrode, electrically connect to the third ECG sensor electrode through a wire in the securing portion, and collect ECG signals from close circuits formed by the first ECG sensor electrode, the second ECG sensor electrode, and the third ECG sensor electrode.

16 Claims, 7 Drawing Sheets

(51) Int. Cl.
*A61B 5/316* (2021.01)
*A61B 5/318* (2021.01)
*A61B 5/327* (2021.01)

(52) U.S. Cl.
CPC .............. *A61B 5/327* (2021.01); *A61B 5/681* (2013.01); *A61B 5/6843* (2013.01); *A61B 5/7275* (2013.01); *A61B 2562/0209* (2013.01); *A61B 2562/04* (2013.01)

(56) References Cited

U.S. PATENT DOCUMENTS

2014/0143064 A1   5/2014  Tran
2015/0018660 A1*  1/2015  Thomson ............. A61B 5/0404
                                              600/393

FOREIGN PATENT DOCUMENTS

| CN | 102613969 A | 8/2012 |
| CN | 103385711 A | 11/2013 |
| CN | 103845044 A | 6/2014 |
| CN | 104027107 A | 9/2014 |
| CN | 203914894 U | 11/2014 |
| CN | 104665820 A | 6/2015 |
| CN | 104881954 A | 9/2015 |
| CN | 204600458 U | 9/2015 |
| CN | 105595992 A | 5/2016 |

* cited by examiner

ECG SIGNAL COLLECTION AND WEARABLE APPARATUS

CROSS-REFERENCE TO RELATED APPLICATION(S)

This application is a continuation of International Application No. PCT/CN2017/000071, filed on Jan. 3, 2017, which claims priority to Chinese Patent Application No. 201610074311.1, filed on Jan. 29, 2016, the contents of both of which are hereby incorporated by reference in their entireties.

TECHNICAL FIELD

This disclosure relates in general to electrocardiography (ECG) signal collection, and in particular, methods and wearable apparatuses for ECG signal collection.

BACKGROUND

A wearable apparatus can collect single-lead (e.g., Lead I) ECG signals. The ECG signals are diverse in shape: their waveforms can change as a heart rate changes; and the waveforms of the collected ECG signals can change under different times and body conditions. Therefore, the accuracy of the single-lead ECG signal is limited, which might reduce the accuracy of cardiovascular disease detection for a user.

SUMMARY

Disclosed herein are methods and apparatuses for ECG signal collection at a wearable device for a user.

In an aspect, a wearable apparatus is disclosed for ECG signal collection. The wearable apparatus includes a main body, a securing portion, and an electrocardiography (ECG) sensor. The main body includes a first ECG sensor electrode provided on a side of the main body away from a wearing position of an individual and a second ECG sensor electrode provided on a side of the main body close to the wearing position. The securing portion includes a third ECG sensor electrode provided on a side of the securing portion away from the wearing position. The ECG sensor is provided in the main body and configured to electrically connect to the first ECG sensor electrode and the second ECG sensor electrode, electrically connect to the third ECG sensor electrode through a wire in the securing portion, and collect ECG signals from close circuits formed by the first ECG sensor electrode, the second ECG sensor electrode, and the third ECG sensor electrode.

In another aspect, a method is disclosed for collecting ECG signals for an individual of a wearable apparatus. The method includes determining, by an ECG sensor, a three-lead ECG signal by collecting ECG signals from close circuits formed by a first ECG sensor electrode, a second ECG sensor electrode, and a third ECG sensor electrode, and receiving, by a microcontroller unit (MCU), the three-lead ECG signal, wherein the wearable apparatus comprises the first ECG sensor electrode, the second ECG sensor electrode, the third ECG sensor electrode, the ECG sensor, and the MCU.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1A:
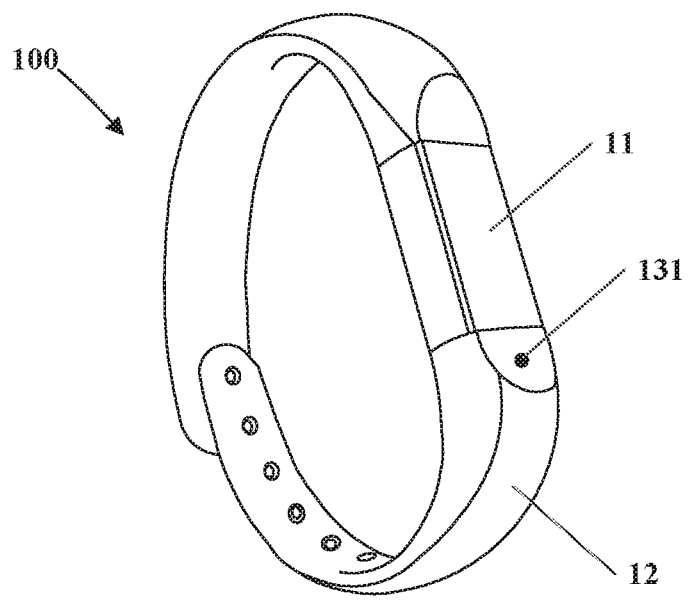
FIG. 1A is a diagram of an example wearable apparatus.
Figure 1B:
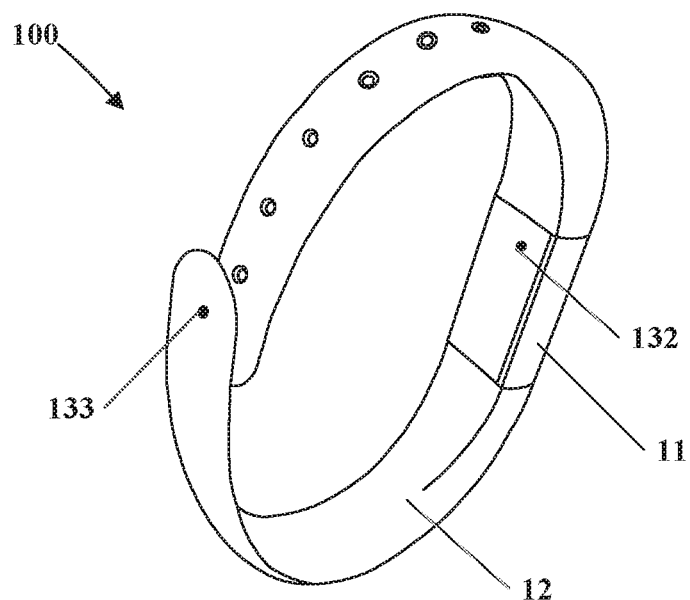
FIG. 1B is another diagram of an example wearable apparatus.

FIG. 1A shows a diagram of an example wearable apparatus 100 according to an implementation of this disclosure. FIG. 1B shows another diagram of the wearable apparatus 100. As shown in FIGS. 1A-1B, the wearable apparatus 100 includes a main body 11 and a securing portion 12 (e.g., a wrist band). The main body 11 includes a first ECG sensor electrode 131 and a second ECG sensor electrode 132. For example, the first ECG sensor electrode 131 can be provided on a surface of the main body 11 away from a wearing position of an individual. The second ECG sensor electrode 132 can be provided on a surface of the main body 11 close to the wearing position of the individual (e.g., a wrist). The securing portion 12 includes a third ECG sensor electrode 133 provided on a side away from the wearing position. The wearable apparatus 100 can further include an ECG sensor (not shown) provided within the main body 11. The ECG sensor can electrically connect to the first ECG sensor electrode 131 and the second ECG sensor electrode 132. The third ECG sensor electrode 133 can also electrically to the ECG sensor via a wire (not shown) inside the securing portion 12 (e.g., a wrist band).

In an implementation, the first ECG sensor electrode 131 and the second ECG sensor electrode 132 can form a first close circuit, from which the ECG sensor can collect a Lead I signal. The second ECG sensor electrode 132 and the third ECG sensor electrode 133 can form a second close circuit, from which the ECG sensor can collect a Lead II signal. The third ECG sensor electrode 133 and the first ECG sensor electrode 131 can form a third close circuit, from which the ECG sensor can collect a Lead III signal.

In some implementations, the wearable apparatus 100 can further include a microcontroller unit (MCU) and a communication interface. For example, the MCU can be provided within the main body 11 and electrically connected to the ECG sensor for receiving an ECG signal collected by the ECG sensor. The communication interface can electrically connect to the MCU, and the MCU can send a three-lead ECG signal to a host device via the communication interface.

In an implementation, the ECG sensor can detect whether any of the first ECG sensor electrode 131, the second ECG sensor electrode 132, and the third ECG sensor electrode 133 is in a detached state. For example, when the ECG sensor detects an ECG sensor electrode is detached, the MCU can be configured to set a lead signal transmitted in a data channel corresponding to the detached ECG sensor electrode to be zero.

In an implementation, the first ECG sensor electrode 131, the second ECG sensor electrode 132, and the third ECG sensor electrode 133 can interconnect to form three close circuits. From the three close circuits, the ECG sensor can collect respective ECG signals corresponding to the three close circuits and obtain a three-lead ECG signal. By using the three-lead ECG signal, it is possible to ensure the diversity of the collected ECG signals, increase the information contained in the ECG signals, improve the accuracy of the obtained ECG signals, and further improve the accuracy of cardiovascular disease detection.

Figure 2:
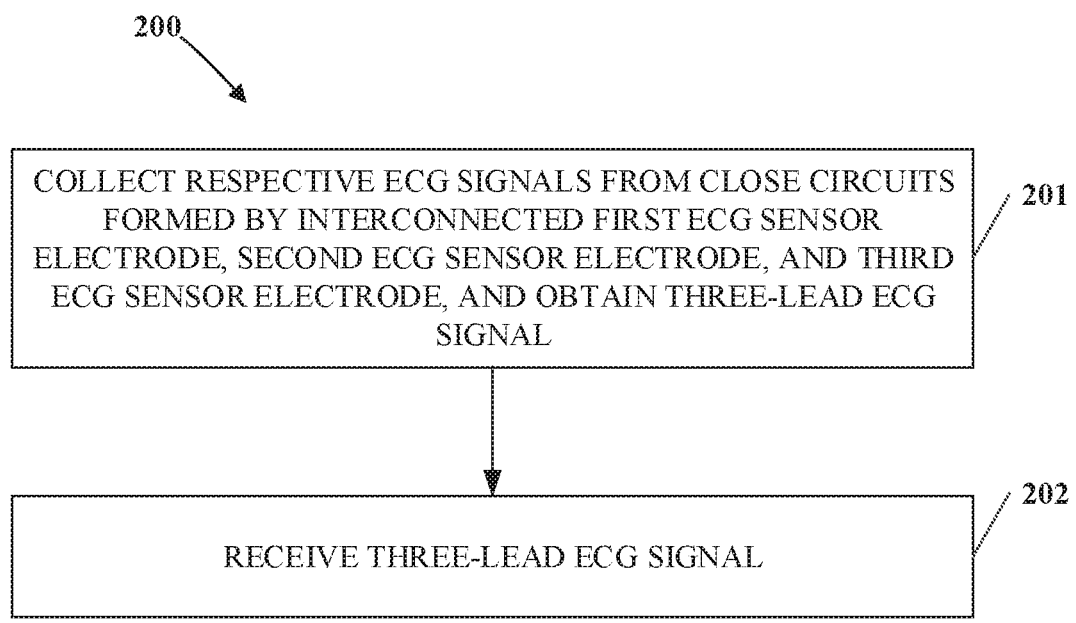
FIG. 2 is a flowchart of an example process for ECG signal collection according to an implementation of this disclosure.

FIG. 2 is a flowchart of an example process 200 for ECG signal collection according to an implementation of this disclosure. In addition to FIG. 2, the process 200 will be described based on FIGS. 1A and 1B as well. As shown in FIG. 2, the process 200 includes operations 201-202.

At the operation 201, the ECG sensor collects respective ECG signals from three close circuits formed by the interconnected first ECG sensor electrode 131, second ECG sensor electrode 132, and third ECG sensor electrode 133, and obtain a three-lead ECG signal.

At the operation 202, the MCU receives the three-lead ECG signal via the ECG sensor.

To ease explanation without causing any ambiguity, implementations of this disclosure will be described hereinafter using an example in which a user wears the wearable apparatus on the left hand. As shown in FIGS. 1A and 1B, at the operation 201, when the user is wearing the wearable apparatus, skin of the left hand of the user can contact the second ECG sensor electrode 132. For example, when the user contacts the first ECG sensor electrode 131 with the right hand (e.g., a finger), the first ECG sensor electrode 131 and the second ECG sensor electrode 132 can form a first close circuit through the human body of the user, and the ECG sensor in the main body 11 of the wearable apparatus can receive a Lead I signal corresponding to the first close circuit. For another example, when the user contacts the third ECG sensor electrode 133 with the left leg and contacts the first ECG sensor electrode 131 with the right hand, the third ECG sensor electrode 133 and the first ECG sensor electrode 131 can form a second close circuit through the human body of the user, and the ECG sensor in the main body 11 of the wearable apparatus can receive a Lead III signal corresponding to the second close circuit. For another example, when the user contacts the third ECG sensor electrode 133 with the left leg and contacts the second ECG sensor electrode 132 with the left hand, the third ECG sensor electrode 133 and the second ECG sensor electrode 132 can form a third close circuit through the human body of the user, and the ECG sensor in the main body 11 of the wearable apparatus can receive a Lead II signal corresponding to the third close circuit.

In an implementation, when the MCU receive the three-lead ECG signal via the ECG sensor, disease detection techniques based on the three-lead ECG signal can be used to determine a disease (e.g., a cardiovascular disease) or a disease type for the user of the wearable apparatus. The three-lead ECG signal includes the Lead I, Lead II, and Lead III ECG signal. In another implementation, the MCU can send the three-lead ECG signal to a host device (e.g., a server, an electronic device, or a cell phone) via the communication interface, and the host device can determine a disease (e.g., a cardiovascular disease) or a disease type for the user of the wearable apparatus. The details of the disease detection will not be further described in this disclosure.

As described above, in this disclosure, the first ECG sensor electrode 131, the second ECG sensor electrode 132, and the third ECG sensor electrode 133 can interconnect to form three close circuits, and the ECG sensor can collect the respective ECG signals from the three close circuits to obtain a three-lead ECG signal. By using the three-lead ECG signal, the collected ECG signal can have diversified forms and shapes, the information contained in the ECG signal can be increased, the accuracy of the collected ECG signal can be improved, and the accuracy of cardiovascular disease detection can be increased.

Figure 3A:
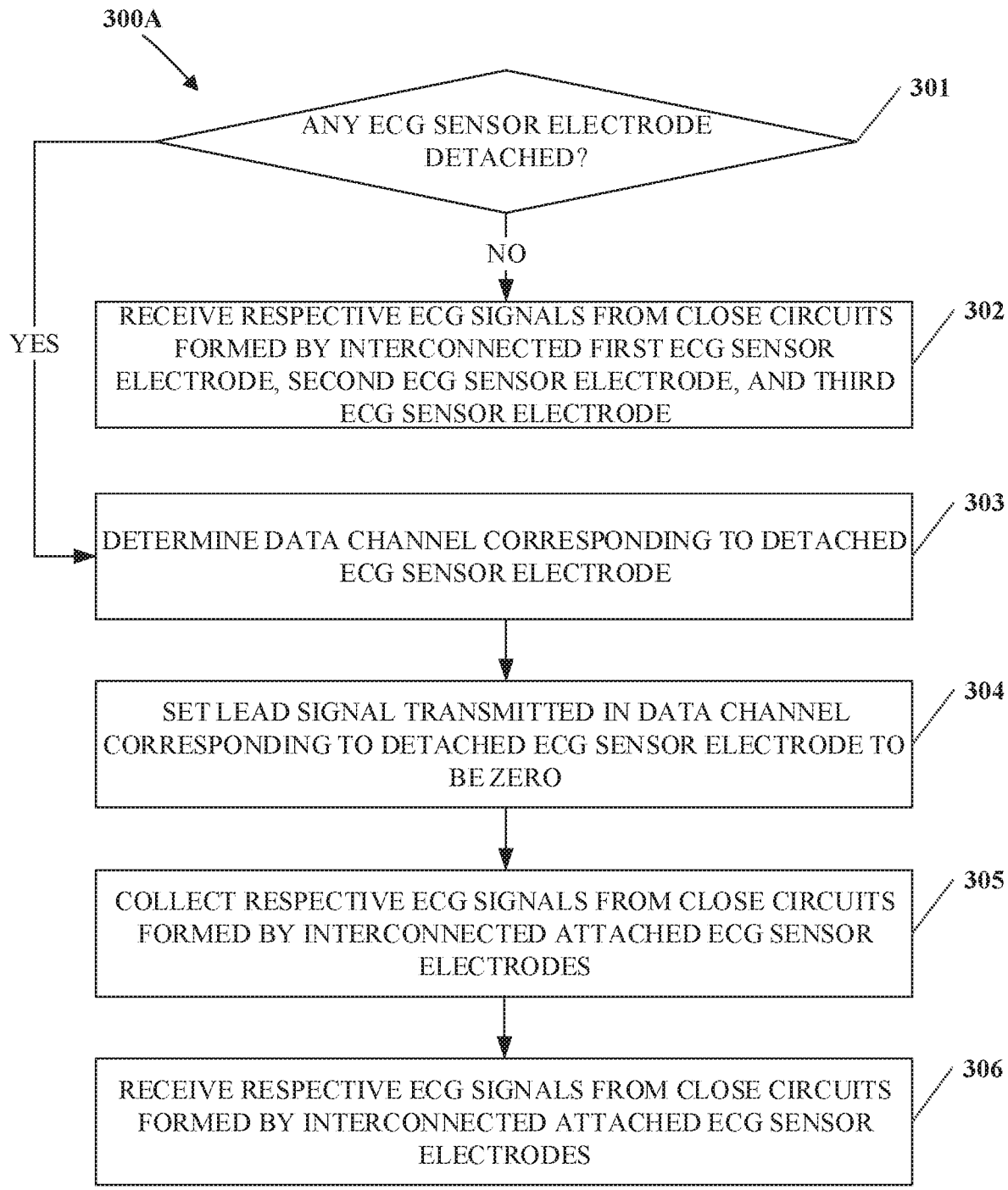
FIG. 3A is a flowchart of another example process for ECG signal collection according to an implementation of this disclosure.
Figure 3B:
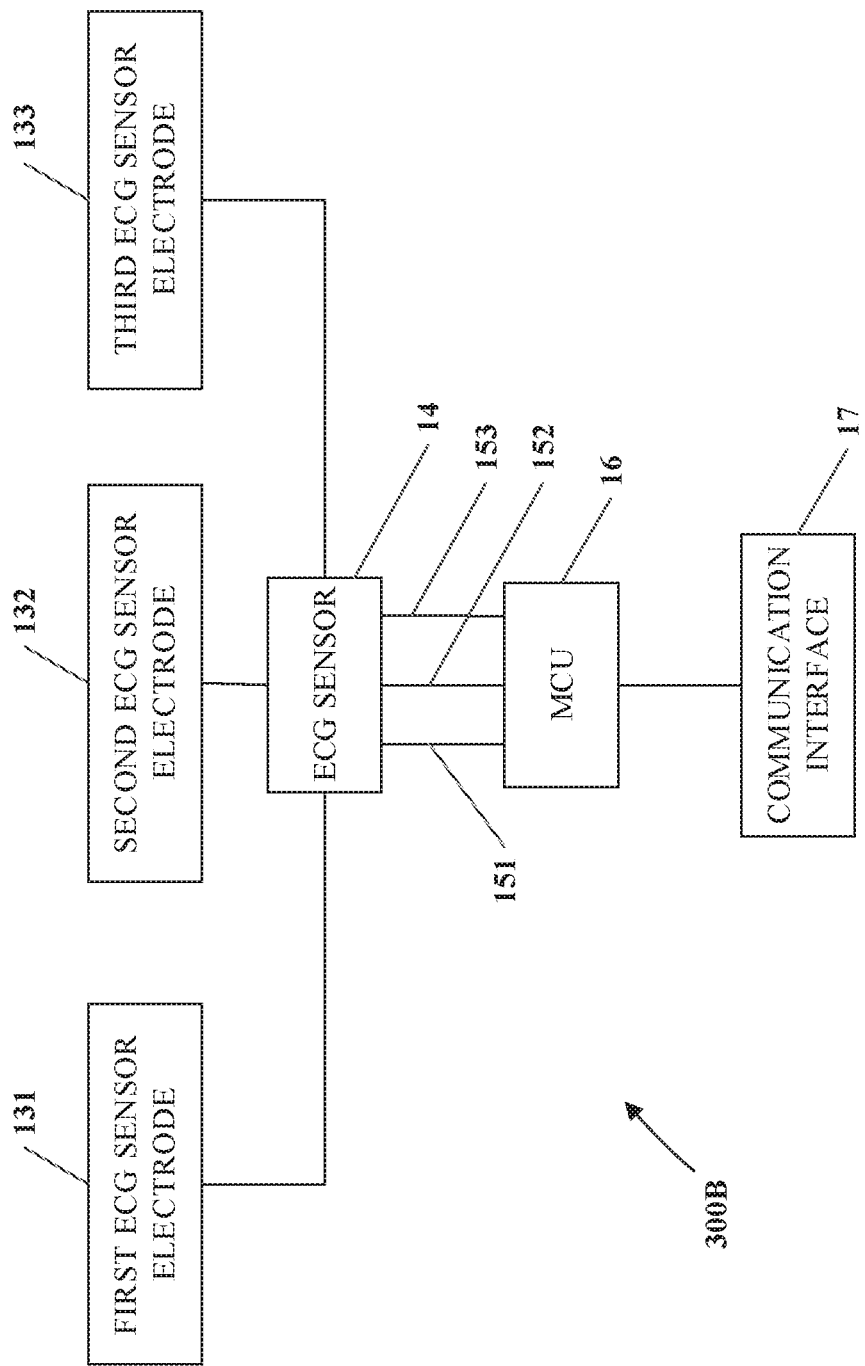
FIG. 3B is a diagram of an example data channel for ECG signal collection according to an implementation of this disclosure.

FIG. 3A is a flowchart of another example process 300A for ECG signal collection according to an implementation of this disclosure. FIG. 3B is a diagram of an example data channel 300B for the process 300A. In addition to FIGS. 3A and 3B, the process 300A will be described based on FIGS. 1A and 1B as well. As shown in FIG. 3A, the process 300A includes operations 301-306.

At the operation 301, an ECG sensor 14 determines whether any of the first ECG sensor electrode 131, the second ECG sensor electrode 132, and the third ECG sensor electrode 133 is detached (e.g., detached from the skin of the user). When no ECG sensor electrode is determined as detached, the process 300A proceeds to the operation 302. When there is at least one ECG sensor electrode being determined as detached, the process 300A proceeds to the operation 303.

At the operation 302, the ECG sensor 14 receives respective ECG signals from three close circuits formed by the interconnected first ECG sensor electrode 131, second ECG sensor electrode 132, and third ECG sensor electrode 133.

At the operation 303, when an ECG sensor electrode is determined as detached, the ECG sensor 14 determines a data channel corresponding to the detached ECG sensor electrode.

At the operation 304, an MCU 16 sets a lead signal transmitted in the data channel corresponding to the detached ECG sensor electrode to be zero.

At the operation 305, the ECG sensor 14 collects respective ECG signals from close circuits formed by interconnected attached (e.g., attached to the skin of the user) ECG sensor electrodes.

At the operation 306, the MCU 16 receives, via the ECG sensor 14, the respective ECG signals from the close circuits formed by the interconnected attached ECG sensor electrodes.

In an implementation, at the operations 301 and 302, it can be determined whether there is any ECG sensor electrode in a detached state by detecting whether any close circuit can be formed between the first ECG sensor electrode 131, the second ECG sensor electrode 132, and third ECG sensor electrode 133. For example, when the right hand of the user detaches from the first ECG sensor electrode 131, the close circuit formed between the first ECG sensor electrode 131 and the second ECG sensor electrode 132 is opened, and the close circuit formed between the first ECG sensor electrode 131 and the third ECG sensor electrode 133 is also opened. In this example, the ECG sensor 14 cannot detect any Lead I or Lead III ECG signal, by which the ECG sensor 14 can further determine that the first ECG sensor electrode 131 is detached.

Details of the operation 303 have been described in implementations of FIG. 2 and will not be further described hereinafter.

At the operations 304-306, as shown in FIG. 3B, the Lead I ECG signal can be transmitted in a data channel 151, the Lead II ECG signal can be transmitted in a data channel 152, and the Lead III ECG signal can be transmitted in a data channel 153. For example, when the first ECG sensor electrode 131 is detached, the ECG sensor 14 cannot send any ECG signal to the MCU 16 via the data channel 151 or the data channel 153. To reduce noise interference with the MCU 16 and decrease power consumption of the MCU 16, the MCU 16 can set the lead signals transmitted in the data channel 151 and the data channel 153 to be zeroes.

In this example, the ECG sensor 14 can collect the Lead II ECG signal via the close circuit formed by the third ECG sensor electrode 133 and the second ECG sensor electrode 132, and send the Lead II ECG signal to the MCU 16 via the data channel 152. Based on the Lead II ECG signal, the MCU 16 can detect a cardiovascular disease type for the user of the wearable apparatus, or send the Lead II ECG signal via a communication interface 17 to a host device (e.g., an electronic device or a server) for disease type detection based on the Lead II ECG signal.

In this implementation, the user of the wearable apparatus can contact different ECG sensor electrodes to obtain ECG signals from different leads, by which the flexibility of ECG signal collection can increase. By setting the lead signal to be zero via the MCU for the data channel corresponding to the detached ECG sensor electrode, the noise interference with the MCU and the power consumption of the MCU can be reduced.

Figure 4:
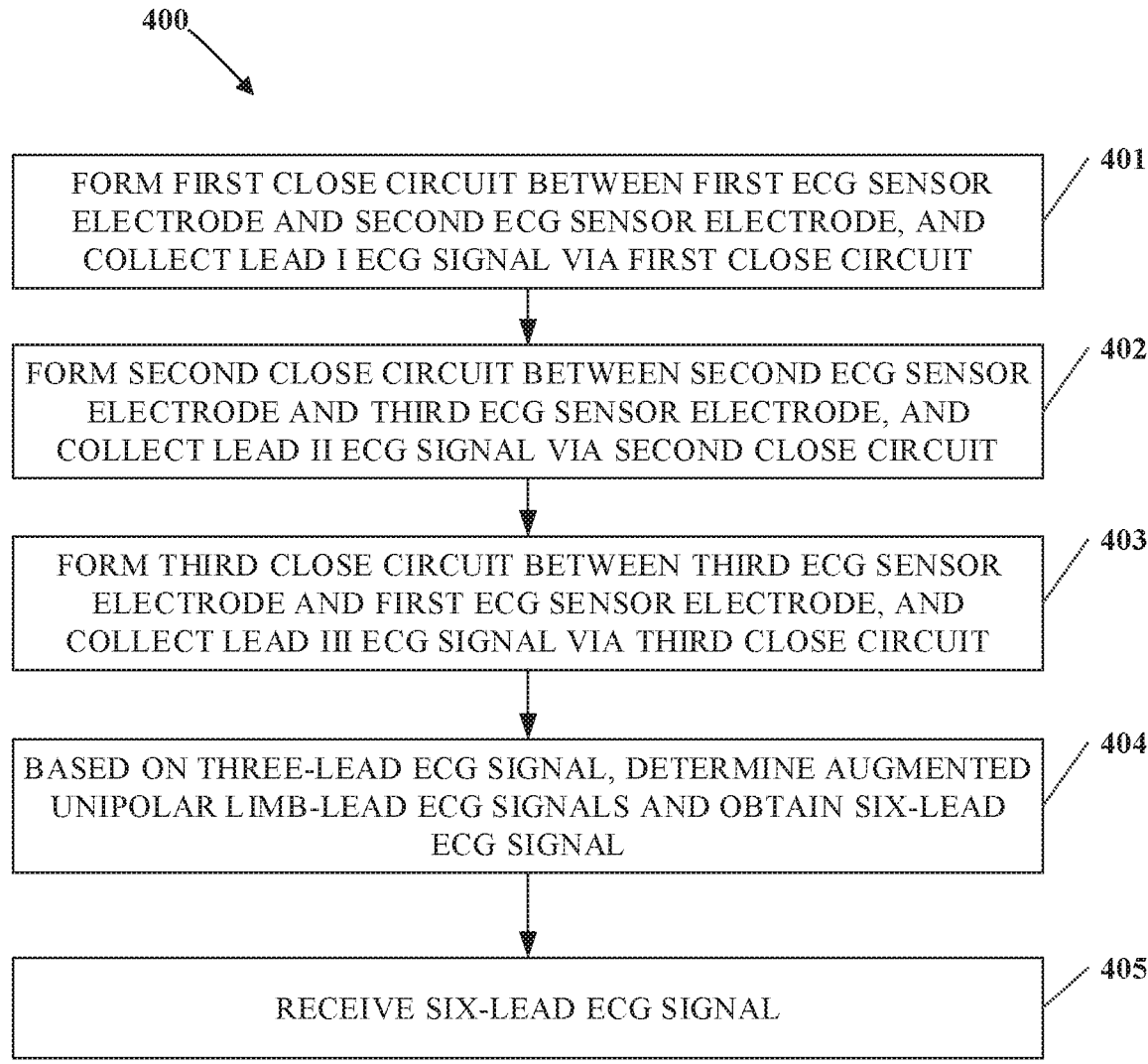
FIG. 4 is a flowchart of another example process for ECG signal collection according to an implementation of this disclosure.

FIG. 4 is a flowchart of an example process 400 for ECG signal collection according to an implementation of this disclosure. As shown in FIG. 4, the process 400 includes the operations 401-405.

At the operation 401, a first ECG sensor electrode and a second ECG sensor electrode form a first close circuit, and an ECG sensor collects a Lead I ECG signal via the first close circuit.

At the operation 402, the second ECG sensor electrode and a third ECG sensor electrode form a second close circuit, and the ECG sensor collects a Lead II ECG signal via the second close circuit.

At the operation 403, the third ECG sensor electrode and the first ECG sensor electrode form a third close circuit, and the ECG sensor collects a Lead III ECG signal via the third close circuit.

At the operation 404, based on the three-lead ECG signal, an MCU determines augmented unipolar limb-lead ECG signals for the user of the wearable apparatus, and obtains a six-lead ECG signal.

At the operation 405, the MCU receives the six-lead ECG signal via the ECG sensor.

It should be noted that the operations 401-403 can be performed in any order or sequence. For example, when detecting any two of the ECG sensor electrodes forming a close circuit, the corresponding operation can be performed.

At the operation 404, after obtaining the three-lead ECG signal from the operations 401-403, the augmented unipolar limb-lead ECG signals (aVR, aVL, and aVF) for the user of the wearable apparatus can be determined in accordance with the relationships as shown in Table 1, based on which the six-lead ECG signal (e.g., I, II, III, aVR, aVL, and aVF) can be determined.

TABLE 1

| Lead | Measurement | Note |
| --- | --- | --- |
| I | LA-RA | LA: left hand, RA: right hand |
| II | LL-LA | LL: left leg, LA: left hand |
| III | LL-RA | LL: left leg, RA: right hand |
| aVR | RA − 0.5 (LA + LL) | |
| aVL | LA − 0.5 (RA + LL) | |
| aVF | LL − 0.5 (RA + LA) | |

According to implementations of this disclosure, compared with implementations using a single-lead (e.g., Lead I), the ECG signals can be obtained more easily with stronger signal strength. Based on the Lead I, -II, and -III ECG signals, a six-lead ECG signal can be determined, which can increase the accuracy of the ECG signals and promote ECG signal usage in the technical field of wearable apparatuses.

In some implementations, based on the six-lead ECG signal, the MCU can detect a cardiovascular disease type for the user of the wearable apparatus. The MCU can also send the six-lead ECG signal to a host device (e.g., a server, an electronic device, or a cell phone) via a communication interface, and the host device can determine a disease (e.g., a cardiovascular disease) or a disease type for the user of the wearable apparatus. By determining the cardiovascular disease type using the host device, the power consumption of the wearable apparatus can be reduced, and the computation complexity at the wearable apparatus can be lowered.

Corresponding to the above-described methods and processes, a control logic for ECG signal collection is also provided in this disclosure. Any component, module, functional block, or unit of the control logic described herein can be implemented as hardware, firmware or software. The hardware, firmware or software for the control logic can include machine-readable instructions. The input and output data of each module of the control logic during operation of the methods and processes can be passed to or from any other module of the control logic. For example, the control logic can be used at a wearable apparatus. In some implementations, the wearable apparatus can include a processor, an ECG sensor, a first ECG sensor electrode, a second ECG sensor electrode, a third ECG sensor electrode, and a machine-readable storage medium. In some implementations, for example, the processor can include an MCU, and the MCU can connect to the machine-readable storage medium via an internal bus. In some implementations, the wearable apparatus can further include a communication interface configured to communicate with another device or component.

In various implementations, the machine-readable storage medium can include a random access memory (RAM), a read-only memory (ROM), a volatile storage device, a non-volatile storage device, a flash drive, or any combination of any non-transitory storage media.

Figure 5:
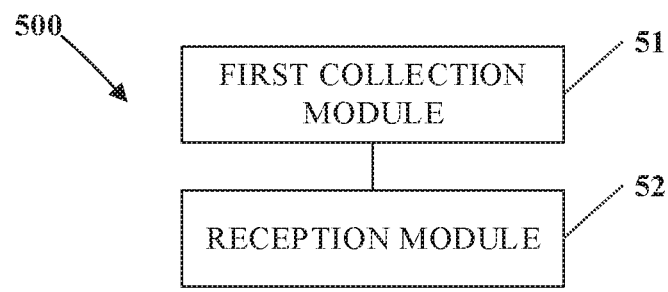
FIG. 5 is a block diagram of an example control logic for ECG signal collection according to an implementation of this disclosure.

The machine-readable storage medium can store machine-executable instructions corresponding to the control logic for ECG signal collection. FIG. 5 is a block diagram of an example control logic 500 for ECG signal collection according to an implementation of this disclosure. Based on functions, the control logic 500 can include a first collection module 51 and a reception module 52.

In an implementation, the first collection module 51 can be configured to control the ECG sensor to collect respective ECG signals from three close circuits formed between the interconnected first ECG sensor electrode, second ECG sensor electrode, and third ECG sensor electrode, and obtain a three-lead ECG signal.

The reception module 52 can be configured to receive the three-lead ECG signal via the first collection module 51.

In an implementation, the control logic 500 can further include a first detection module 53. The first detection module 53 can be configured to determine a cardiovascular disease type for the user of the wearable apparatus based on the three-lead ECG signal.

Figure 6:
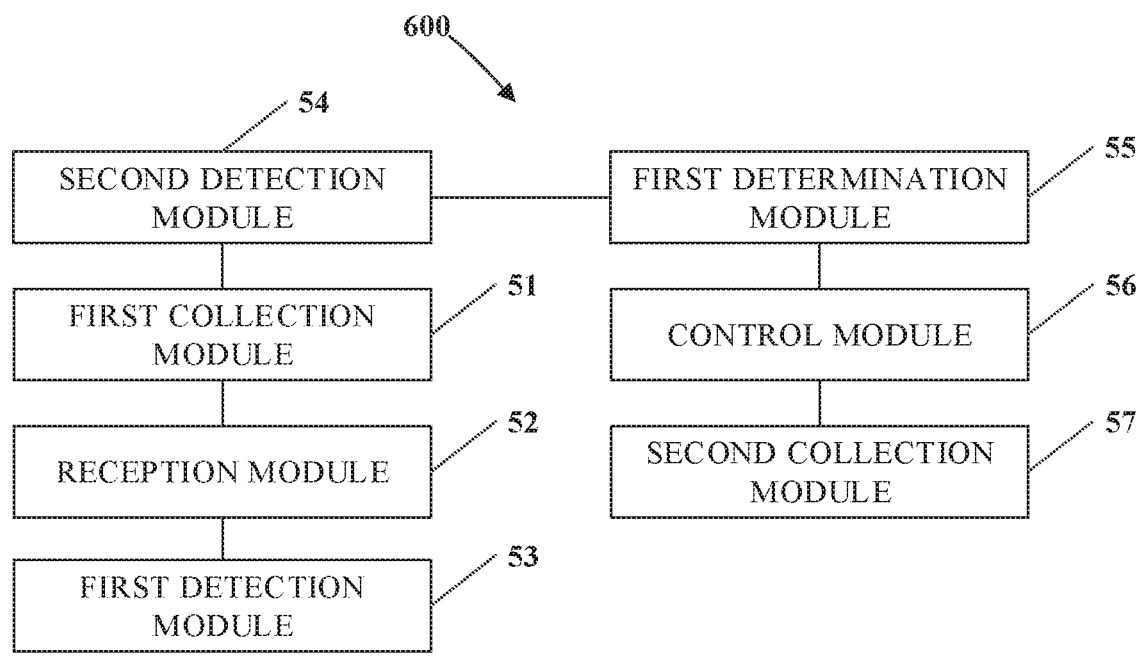
FIG. 6 is a block diagram of another example control logic for ECG signal collection according to an implementation of this disclosure.

FIG. 6 is a block diagram of an example control logic 600 for ECG signal collection according to an implementation of this disclosure. As shown in FIG. 6, in addition to the control logic 500, the control logic 600 further includes a second detection module 54, a first determination module 55, a control module 56, and a second collection module 57.

In an implementation, the second detection module 54 can be configured to detect whether any of the first ECG sensor electrode, the second ECG sensor electrode, and the third ECG sensor electrode is detached.

When the second detection module 54 detects no ECG sensor electrode being detached, the first collection module 51 can collect respective ECG signals via the ECG sensor from the three close circuits formed by the interconnected first ECG sensor electrode, second ECG sensor electrode, and third ECG sensor electrode.

When the second detection module 54 detects an ECG sensor electrode is detached, the first determination module 55 can be configured to determine a data channel corresponding to the detached ECG sensor electrode.

The control module 56 can be configured to set, via an MCU, a lead signal transmitted in the data channel corresponding to the detached ECG sensor electrode determined by the first determination module 55 to be zero.

The second collection module 57 can be configured to collect respective ECG signals via the ECG sensor from the close circuits formed by the interconnected attached ECG sensor electrodes.

Figure 7:
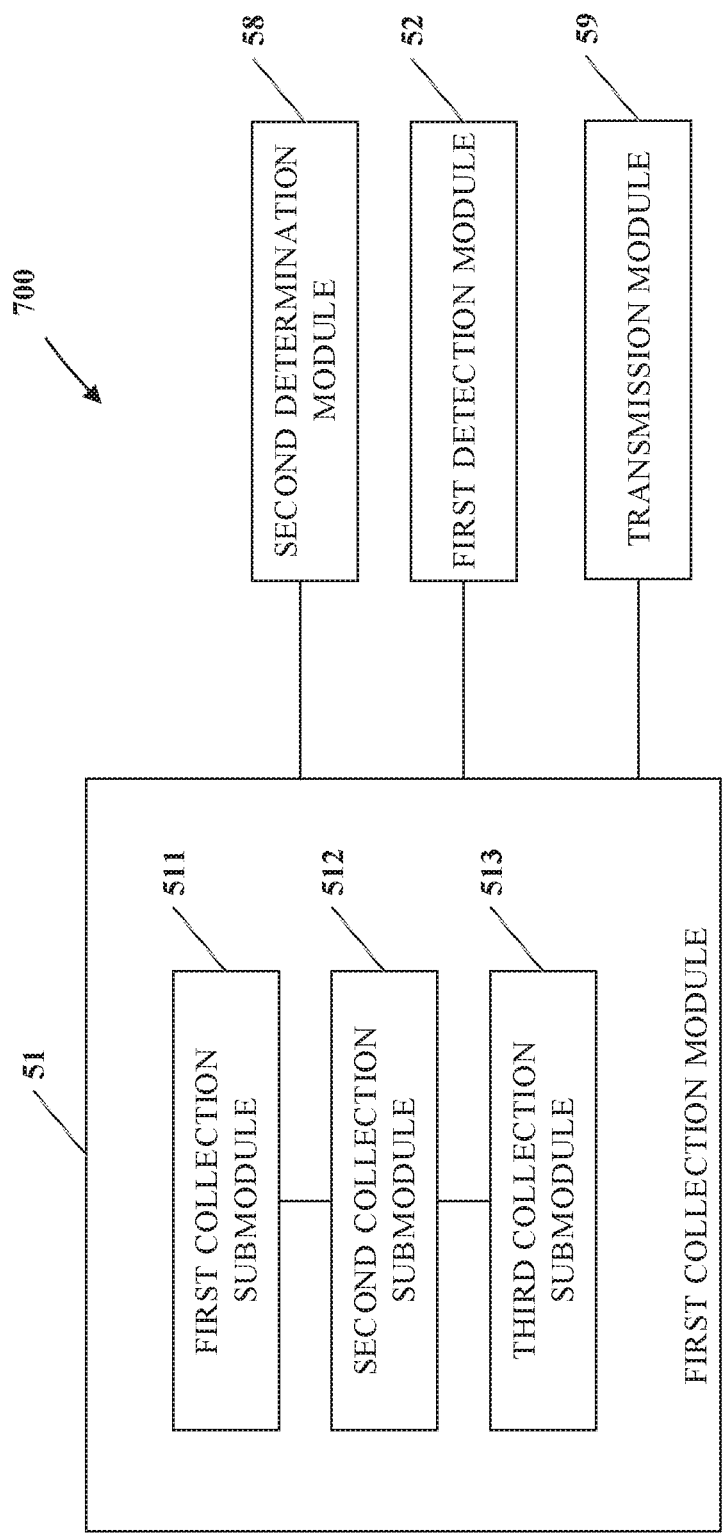
FIG. 7 is a block diagram of a third example control logic for ECG signal collection according to an implementation of this disclosure.

FIG. 7 is a block diagram of an example control logic 700 for ECG signal collection according to an implementation of this disclosure. As shown in FIG. 7, in addition to FIGS. 5 and 6, the first collection module 51 further includes a first collection submodule 511, a second collection submodule 512, and a third collection submodule 513.

In an implementation, the first collection submodule 511 can be configured to collect a Lead I ECG signal from a first close circuit formed by the first ECG sensor electrode and the second ECG sensor electrode.

The second collection submodule 512 can be configured to collect a Lead II ECG signal from a second close circuit formed by the second ECG sensor electrode and the third ECG sensor electrode.

The third collection submodule 513 can be configured to collect a Lead III ECG signal from a third close circuit formed by the third ECG sensor electrode and the first ECG sensor electrode.

In an implementation, the control logic 700 can further include a second determination module 58.

Based on the three-lead ECG signal collected by the first collection module 51, the second determination module 58 can be configured to determine augmented unipolar limb-lead ECG signals for the user of the wearable apparatus, and determine a six-lead ECG signal.

In an implementation, the control logic 700 can further include a transmission module 59.

The transmission module 59 can be configured to send the three- or six-lead ECG signal collected by the first collection module 51 to a host device, and the host device can determine a cardiovascular disease type for the user of the wearable apparatus based on the three- or six-lead ECG signal.

The control logics and operations performed by their units or components have been described in previous implementations of the methods and processes, and will not be further described hereinafter.

It should be understood that although this disclosure uses the terms of "first, second, third," etc. for description, such description should not be limited to those terms. On the contrary, those terms are used only to distinguish the same type of information from each other. For example, without departing from the scope of this disclosure, the first information can also be referred to as the second information, and, similarly, the second information can also be referred to as the first information. Depending on the context, the words "if," as used herein can be interpreted as "when" or "while" or "in response to."

The terms "comprise" or "include" or any other variant thereof are intended to encompass a non-exclusive inclusion, such that the processes, methods, articles, or apparatuses comprising a series of elements include not only the explicitly listed elements, but also other elements not explicitly listed, or elements that are inherent to such processes, methods, articles, or apparatuses.

In addition, the articles "a" and "an" as used in this application and the appended claims should generally be construed to mean "one or more" unless specified otherwise or clear from context to be directed to a singular form. In the absence of more restrictions, the elements defined by the statement "including a . . . " do not preclude the existence of additional same elements in the processes, methods, articles, or devices that includes the element.

While the disclosure has been described in connection with certain implementations and embodiments, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A wearable apparatus, comprising:
   a main body, comprising a first ECG sensor electrode provided on a side of the main body away from a wearing position of an individual and a second ECG sensor electrode provided on a side of the main body close to the wearing position;
   a securing portion, comprising a third ECG sensor electrode provided on a side of the securing portion away from the wearing position; and
   an electrocardiography (ECG) sensor, provided in the main body and configured to:
      electrically connect to the first ECG sensor electrode and the second ECG sensor electrode,
      electrically connect to the third ECG sensor electrode through a wire in the securing portion,
      determine at least one ECG sensor electrode of the first, second and third electrodes that is detached from the individual and at least another ECG sensor electrode of the first, second and third electrodes that is attached to the individual and determine a data channel corresponding to the detached ECG sensor electrode; and a microcontroller unit (MCU), provided in the main body, and configured to electrically connect to the ECG sensor and setting a lead signal transmitted through the data channel corresponding to the detached ECG sensor electrode to be zero to reduce power consumption and noise interference and receive the ECG signal from the closed circuits formed by the at least another ECG sensor electrode attached to the individual.

2. The wearable apparatus of claim 1, wherein the ECG sensor is further configured to:

collect a Lead I ECG signal from a first close circuit formed by the first ECG sensor electrode and the second ECG sensor electrode, collect a Lead II ECG signal from a second close circuit formed by the second ECG sensor electrode and the third ECG sensor electrode, and collect a Lead III ECG signal from a third close circuit formed by the third ECG sensor electrode and the first ECG sensor electrode.

3. The wearable apparatus of claim 1, further comprising:

a communication interface, configured to electrically connect to the MCU, wherein the MCU is configured to send the ECG signals to a host device using the communication interface.

4. A wearable apparatus of claim 1, wherein the MCU is further configured to:

determine a cardiovascular disease type for the individual based on the three-lead ECG signal based on the ECG signals from close circuits formed by the first, second and third ECG sensor electrodes.

5. The wearable apparatus of claim 1, wherein the MCU is further configured to:

determine a six-lead ECG signal by determining augmented unipolar limb-lead ECG signals based on the three-lead ECG signal; and determine a cardiovascular disease type for the individual based on the six-lead ECG signal.

6. A method of collecting electrocardiogram (ECG) signals for an individual of a wearable apparatus, comprising:

positioning the wearable apparatus on the individual, wherein the wearable apparatus comprises a first ECG sensor electrode, a second ECG sensor electrode, a third ECG sensor electrode, an ECG sensor and a microcontroller unit (MCU);

obtaining, by the ECG sensor, a three-lead ECG signal by collecting ECG signals from closed circuits formed by the first, second and third ECG sensor electrodes;

determine, by the ECG sensor, whether at least one ECG sensor electrode of the first, second, and third sensor electrodes is detached from the individual and at least another one of ECG sensor electrode from the first, second and third sensor electrodes is attached to the individual;

determine, by the ECG sensor, a data channel corresponding to the detached ECG sensor electrode;

setting, by the MCU, a lead signal transmitted through the data channel corresponding to the at least one ECG sensor electrode corresponding to the detached ECG sensor electrode to be zero to reduce power consumption and noise interference; and collecting the ECG signal from the closed circuits formed by the at least another ECG sensor electrode attached to the individual.

7. The method of claim 6, further comprising: determining, by the MCU, a cardiovascular disease type for the individual based on the three-lead ECG signal based on the collected ECG signals from close circuits formed by the first, second and third ECG sensor electrodes.

8. The method of claim 6, further comprising: sending, by a communication interface, the three-lead ECG signal based on the collected ECG signals from closed circuits formed by the first, second and third ECG sensor electrodes.

9. The method of claim 6, further comprising: determining, by the host device, a cardiovascular disease type for the individual based on the three-lead ECG signal based on the collected ECG signals from close circuits formed by the first, second and third ECG sensor electrodes.

10. The method of claim 8, wherein the host device comprises at least one of a server and a phone.

11. The method of claim 6, further comprising: based on a determination that none of the first ECG sensor electrode, the second ECG sensor electrode, and the third ECG sensor electrode is detached from the individual, collecting the ECG signals from the closed circuits formed by the first, second and third ECG sensor electrodes.

12. The method of claim 6, wherein determining the three-lead ECG signal by collecting the ECG signals from the close circuits formed by the first ECG sensor electrode, the second ECG sensor electrode, and the third ECG sensor electrode comprises:

collecting a Lead I ECG signal from a first close circuit formed by the first ECG sensor electrode and the second ECG sensor electrode;

collecting a Lead II ECG signal from a second close circuit formed by the second ECG sensor electrode and the third ECG sensor electrode; and collecting a Lead III ECG signal from a third close circuit formed by the third ECG sensor electrode and the first ECG sensor electrode.

13. The method of claim 6, further comprising:

determining a six-lead ECG signal by determining augmented unipolar limb-lead ECG signals based on the three-lead ECG signal.

14. The method of claim 13, further comprising:

determining, by the MCU, a cardiovascular disease type for the individual based on the six-lead ECG signal.

15. The method of claim 13, further comprising:

sending, by a communication interface, the six-lead ECG signal to a host device, wherein the wearable apparatus comprises the communication interface.

16. The method of claim 15, further comprising:

determining, by the host device, a cardiovascular disease type for the individual based on the six-lead ECG signal.

* * * * *